(12) United States Patent
Najarian et al.

(10) Patent No.: US 8,805,051 B2
(45) Date of Patent: Aug. 12, 2014

(54) IMAGE PROCESSING AND MACHINE LEARNING FOR DIAGNOSTIC ANALYSIS OF MICROCIRCULATION

(75) Inventors: Kayvan Najarian, Glen Allen, VA (US); Rosalyn Stacy Hobson, Richmond, VA (US); Kevin R. Ward, Glen Allen, VA (US); Sumeyra Ummuhan Demir Kanik, Ankara (TR); Nazanin Mirshahi, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 525 days.

(21) Appl. No.: 13/259,414

(22) PCT Filed: Mar. 17, 2010

(86) PCT No.: PCT/US2010/027605
§ 371 (c)(1),
(2), (4) Date: Feb. 24, 2012

(87) PCT Pub. No.: WO2010/117576
PCT Pub. Date: Oct. 14, 2010

(65) Prior Publication Data
US 2012/0269420 A1    Oct. 25, 2012

Related U.S. Application Data

(60) Provisional application No. 61/167,281, filed on Apr. 7, 2009.

(51) Int. Cl.
*G06K 9/00* (2006.01)
*G06T 7/00* (2006.01)
*A61B 5/026* (2006.01)
*A61B 5/00* (2006.01)
*A61B 5/02* (2006.01)
*G06F 19/00* (2011.01)
*G06T 7/20* (2006.01)

(52) U.S. Cl.
CPC ............. *A61B 5/0261* (2013.01); *G06T 7/0097* (2013.01); *A61B 5/412* (2013.01); *G06T 2207/10016* (2013.01); *A61B 5/02007* (2013.01); *G06F 19/345* (2013.01); *A61B 5/726* (2013.01); *G06T 2207/30104* (2013.01); *G06T 2207/20081* (2013.01); *G06T 7/0012* (2013.01); *G06T 7/0081* (2013.01); *G06F 19/321* (2013.01); *G06T 2207/20148* (2013.01); *G06T 7/2053* (2013.01)
USPC ......................................... 382/134; 382/128

(58) Field of Classification Search
USPC .................. 382/100, 128–134; 128/920, 922; 600/101, 109, 112, 114, 117, 118, 139, 600/145, 173, 420, 424, 427, 434
See application file for complete search history.

(56) References Cited

U.S. PATENT DOCUMENTS

2006/0161063 A1    7/2006  Shau
2006/0184037 A1 *  8/2006  Ince et al. ..................... 600/476

(Continued)

*Primary Examiner* — Hadi Akhavannik
*Assistant Examiner* — Mehdi Rashidian
(74) *Attorney, Agent, or Firm* — Whitham Curtis Christofferson & Cook, PC

(57) ABSTRACT

Automated quantitative analysis of microcirculation, such as density of blood vessels and red blood cell velocity, is implemented using image processing and machine learning techniques. Detection and quantification of the microvasculature is determined from images obtained through intravital microscopy. The results of quantitatively monitoring and assessing the changes that occur in microcirculation during resuscitation period assist physicians in making diagnostically and therapeutically important decisions such as determination of the degree of illness as well as the effectiveness of the resuscitation process. Advanced digital image processing methods are applied to provide quantitative assessment of video signals for detection and characterization of the microvasculature (capillaries, venules, and arterioles). The microvasculature is segmented, the presence and velocity of Red Blood Cells (RBCs) is estimated, and the distribution of blood flow in capillaries is identified for a variety of normal and abnormal cases.

12 Claims, 10 Drawing Sheets

(56) References Cited

U.S. PATENT DOCUMENTS

| | | |
|---|---|---|
| 2008/0188962 A1 | 8/2008 | Suryanarayanan et al. |
| 2008/0281205 A1* | 11/2008 | Naghavi et al. ............... 600/458 |
| 2008/0287753 A1 | 11/2008 | Parlikar et al. |
| 2009/0012378 A1* | 1/2009 | Ince ............................... 600/322 |

* cited by examiner

IMAGE PROCESSING AND MACHINE LEARNING FOR DIAGNOSTIC ANALYSIS OF MICROCIRCULATION

CROSS-REFERENCE TO RELATED APPLICATIONS

This application is a 371 of International Application PCT/US2010/027605 filed on Mar. 17, 2010, which claims priority to U.S. Provisional Application 61/167,281 filed on Apr. 7, 2009.

BACKGROUND OF THE INVENTION

1. Field of the Invention

The present invention generally relates to the detection of capillaries and small blood vessels in videos recorded from tissue surfaces, such as the lingual surface and, more particularly, to a system and process for quantitative assessment of video signals for detection and characterization of capillaries in order to monitor and assess changes that occur in microcirculation to assist physicians in making diagnostically and therapeutically important decisions such as determination of the effectiveness of the resuscitation process.

2. Background Description

Knowledge of healthy distribution and circulation of blood in capillaries has been considered as a key factor to assess tissue oxygenation (see, for example, V. Cerný, Z. Turek, and R. Parízková, "Orthogonal polarization spectral imaging: a review," Physiol. Res. 56, 2007). Study of microcirculation has shown potential diagnostic value in diseases such as sepsis (see, for example, R. M. Bateman, M. D. Sharpe, and C. G. Ellis, "Bench-to-bedside review: microvascular dysfunction in sepsis: hemodynamics, oxygen transport and nitric oxide". Crit Care Med 7: 359-373, 2003), chronic ulcers, diabetes mellitus, and hypertension (see, for example, B. I. Levy, G. Ambrosio, A. R. Pries, and H. A. Struijker-Boudier. "Microcirculation in hypertension: a new target for treatment?"Circulation 104:735-740, 2001, and C. Verdant and D. De Backer, "How monitoring of the microcirculation may help us at the bedside", Curr Opin Crit Care 2005, 11(3):240-244). The alteration in microcirculation measures during resuscitation is also of interest of numerous physicians (see, for example, Sala Y, Dubois M. J., D. De Backer, J. Creteur, and J. L. Vincent, "Persistent microcirculatory alterations are associated with organ failure and death in patients with sepsis shock", Crit Care Med 2004, 32:1825-1831, P. E. Spronk, C. Ince, M. J. Gardien, K. R. Mathura, H. M. Oudemans-van Straaten, and D. F. Zandstra, "Nitroglycerin in sepsis shock after intravascular volume resuscitation", Lancet 2002, 360: 1395-1396, and Michael Fries, MD; Weil, Max Harry, MD, PhD, FCCM; Yun-Te Chang, MD; Carlos Castillo, MSEE; Wanchun Tang, MD, FCCM "Microcirculation during cardiac arrest and resuscitation", Crit Care Med 34 (2006), pp. 445-457). A technology that can quantitatively detect and monitor the changes in microcirculation can lead to early detection of these pathological conditions, and therefore better chance of treatment (see, for example, Orsolya Genzel-Boroviczeny, Julia Strotgen, Anthony G. Harris, Konrad Messmer, and Frank Christ, "Orthogonal polarization spectral imaging (OPS): A novel method to measure the microcirculation in term and preterm infants transcutaneously", Pediatr Res 51:386-391, 2002). In particular, in trauma, it is highly desirable to automatically monitor microcirculation during resuscitation and decide when to start and/or stop resuscitation according to real-time quantitative analysis of microcirculation.

Recently developed hardware systems have provided the means to capture video recordings of capillaries in lingual surface. In particular, the two major imaging methods, Orthogonal Polarization Spectral (OPS) imaging (see Genzel-Boroziczeny et al., ibid.) and Side-stream Dark Field (SDF) imaging (see Ince C, "The microcirculation is the motor of sepsis", Critical Care 2005, 9(suppl 4):S13-S19) are being widely employed in the field of clinical microcirculatory research. In this research study, video recordings with high resolution captured by Microscan system were acquired. Despite the advances in the hardware, the lack of effective computational methods to analyze and interpret these images is still the main challenge.

Dobbe et al. proposed a method based on image stabilization, centerline detection and space time diagram (J. G. G. Dobbe, G. J. Streekstra, B. Atasever, R. van Zijderveld and C. Ince, "The measurement of functional microcirculatory density and velocity distributions using automated image analysis", Med Biol Eng Comput. 2008 July; 46(7): 659-670). Pattern recognition techniques were used by Joes Staal et al. to extract ridges (Joes Staal, Michael D. Abrámoff, Meindert Niemeijer, Max A. Viergever, and Bram van Ginneken, "Ridge-Based vessel segmentation in color images of the retina", IEEE Transactions on Medical Imaging, vol. 23, no. 4, pp. 501-509, 2004). Hoover and Goldbaum (Adam Hoover and Michael Goldbaum, "Locating the optic nerve in a retinal image using the fuzzy convergence of the blood vessels", IEEE Tran. on Medical Imaging, Vol. 22, No. 8, August 2003, p. 951-958) utilized fuzzy convergence to extract the optic nerve in images of the ocular fundus. Vermeer et al. (K. A. Vermeer, F. M. Vos, H. G. Lemij, A. M. Vossepoel, "A model based method for retinal blood vessel detection", Comput. Biol. Med., in press. DOI: 10.1016/S0010-4825(03)00055-6, 2003) proposed a model based approach. Artificial intelligence-based approaches were applied by Rost et al. (U. Rost, H. Munkel, and C.-E. Liedtke, "A knowledge based system for the configuration of image processing algorithms", Fachtagung Informations and Mikrosystem Technik, March, 1998).

SUMMARY OF THE INVENTION

An embodiment of the invention detects the presence and density of active capillaries in SDF video recordings, quantitatively monitor and assess the flow of red blood cells in the detected capillaries and quantitatively monitor and assess the changes that occur in microcirculation during treatment of some diseases as well as resuscitation period.

According to an embodiment of the invention, image processing techniques are used to automatically detect capillaries and small blood vessels in order to derive more diagnostically useful information to assist physicians and medical researchers. The system applies advanced digital image processing methods to provide quantitative assessment of video signals for detection and characterization of capillaries. The objective is to segment capillaries, estimate the presence of Red Blood Cells (RBCs), and identify the distribution of blood flow in capillaries for a variety of normal and abnormal cases. Active capillaries are identified. Then, using Functional Capillary Density (FCD), subjects are classified as normal or hemorrhagic stage. A decision-support system aids physicians in diagnosing diseases using calculated quantitative parameters of microcirculation. The invention aims to reduce the human interaction as well as the computation time.

The system is fully-automated and is capable of performing the entire analysis without human intervention; however, it allows for human expert intervention if needed. The technique calculates the indices of Functional Capillary Density (FCD) and Proportion of Perfused Vessels (PPV) to assist physicians and medical researchers in diagnose and treatment of diseases that affect the structure of microcirculation.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The embodiment of the invention is described in terms of a system on which the methods of the invention may be implemented. The system is composed of various imaging components, databases and computational interfaces that one of ordinary skill in the computational arts will be familiar with. The methods of the invention are described with reference to flowcharts which illustrate the logic of the processes implemented. The flowcharts and the accompanying descriptions are sufficient for one of ordinary skill in the computer programming and image processing arts to prepare the necessary code to implement the embodiment of the invention.

Figure 1:
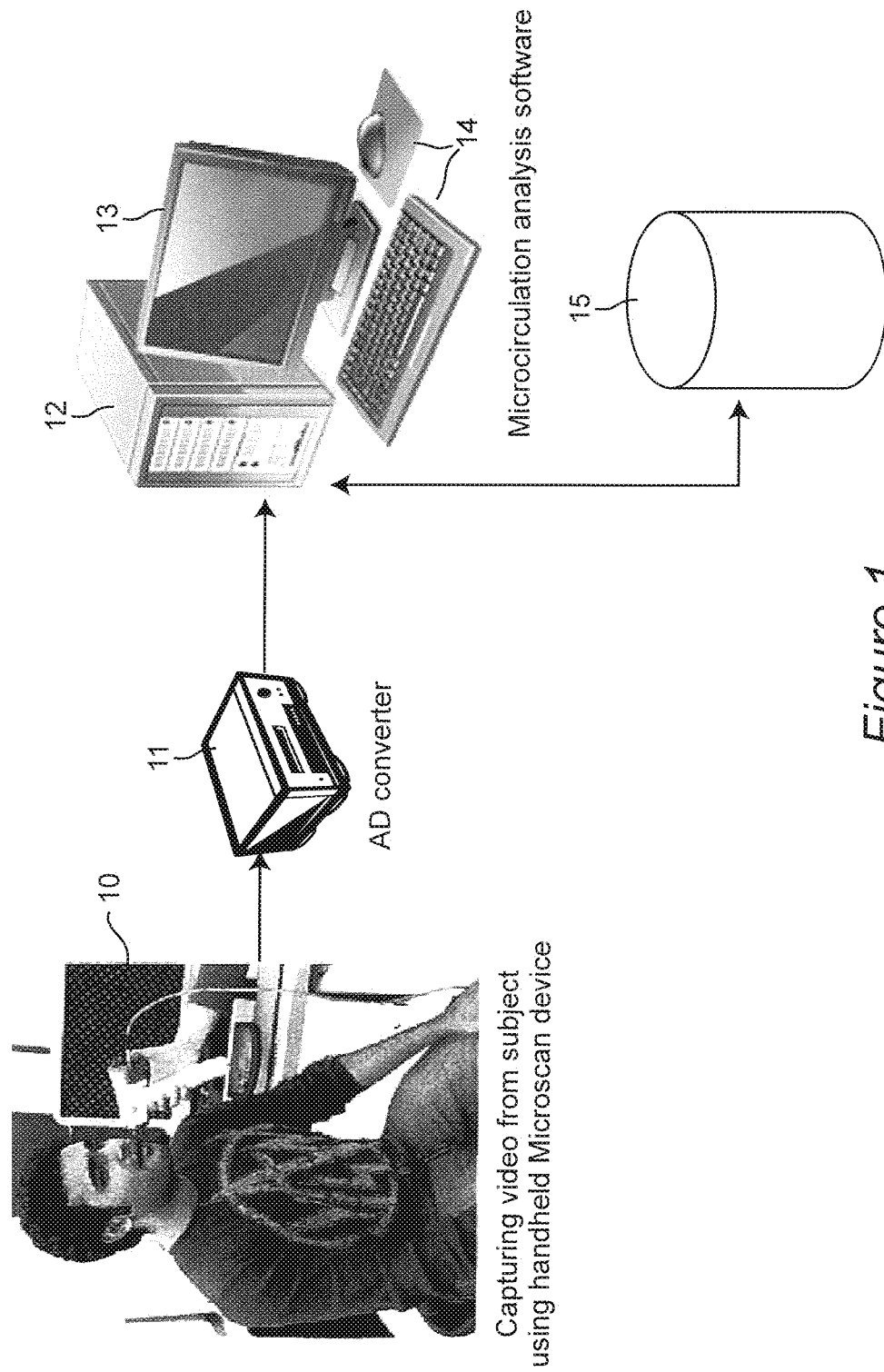
FIG. 1 is a block diagram showing a system which implements an embodiment of the invention.

The following describes the methodology of the algorithm implemented by an embodiment of the invention. The methodology contains two stages: Video stabilization and Segmentation. Referring to FIG. 1, video of capillaries are captured by a handheld microscan device 10. As illustrated, the device is pressed against the patient's tongue to obtain video images of the capillaries and small blood vessels in the lingual surface. While the lingual surface is the preferred surface to obtain these video images because of the profusion of capillaries and small blood vessels in the tongue, other body surfaces could also be used to generate these video images, including but not limited to the ear lobe and whites of the eye. These video images are converted to digital images by analog-to-digital (A/D) converter 11, which are then input to a computer or data processing system, here illustrated as a desk top computer 12. The computer 12 could be connected to a server and other computers through a network (not shown). The computer 12 is provided with a user interface, including a display 13 and keyboard and mouse 14, and is connected to a database 15 for storing patient data. The computer 12 is programmed to first stabilize the digital video images and then to segment the stabilized video images, as will be described in more detail below. The results of the microcirculation analysis which follows stabilization and segmentation are displayed on the display 13, with an indication of diagnostic decisions.

In the training phase, a prior dataset stored in database 15 is used to train the predictive model generated by the computer 12. Machine learning methods are applied to the prior dataset in the decision-support system. More particularly, machine learning techniques, including creating decision trees and extracting rules, are applied to the dataset to generate predictive models of patient condition and/or diseases. These models are used to provide diagnosis and treatment to physicians, assisting them in making rapid and accurate treatment choices for new patients. When the generated model is later used to make diagnostic decisions for a new patient, the same information is collected and used as input. The diagnostic decisions are displayed on display 13, and computer 12 correlates the diagnostic decisions and actions taken by the physician, as input on user interface, with the patient's records, which are stored in the patient's record in database 15.

The imaging technique used by the embodiment of the invention allows observing capillaries only if Red Blood Cells (RBCs) exist. The hemoglobin protein carried by RBCs absorbs the incident wavelength used by SDF system (see Genzel-Boroviczemy et al., ibid.). Therefore, RBCs bounded with vessel walls are considered as vessels. Two main problems need to be addressed. First, the video files captured from the surface of the tongue have very low contrast, and therefore need to be improved in quality at the image processing level. Secondly, videos are not stable due to the movements of the camera and/or the subject. To deal with the movements, digital stabilization algorithm and image registration techniques are applied. Because of low contrast, it is not a trivial task to identify which pixel is a background pixel and which one belongs to a capillary.

Figure 2:
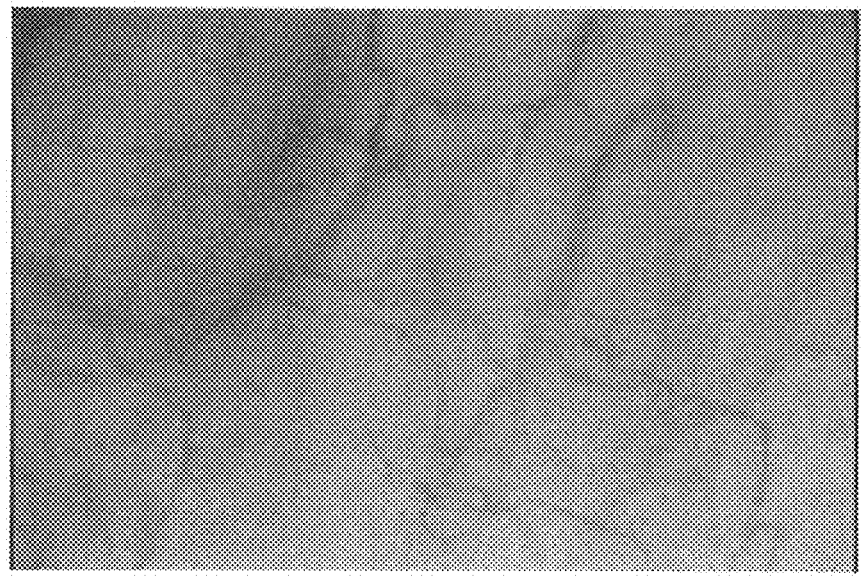
FIG. 2 shows an original video frame of blood vessels from a video of the tongue surface.
Figure 3:
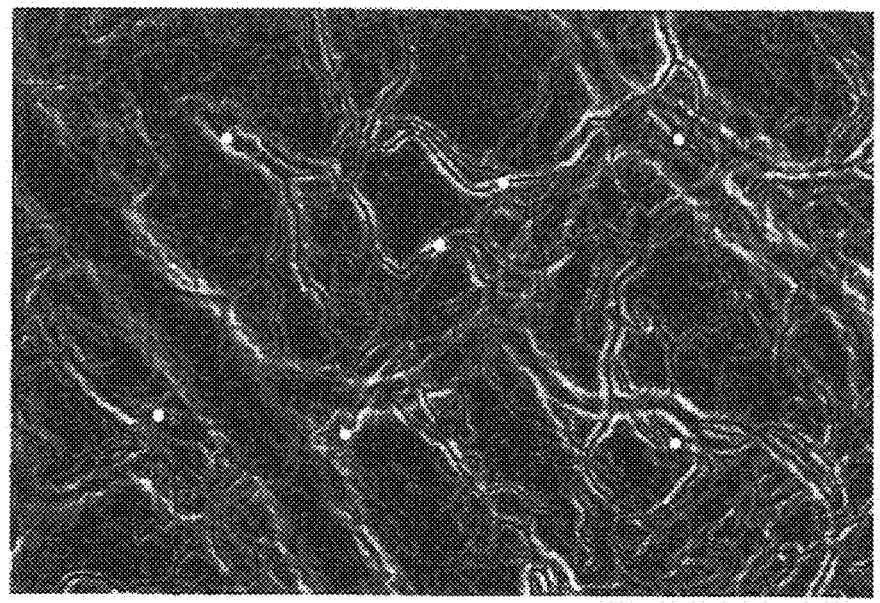
FIG. 3 shows the result of the stabilization step on the video frame of FIG. 2 as implemented by an embodiment of the invention.

To illustrate the processes implemented by an embodiment of the invention, an original video frame of a capillary image can be seen at FIG. 2. FIG. 3 illustrates the result of the stabilization, as implemented by an embodiment of the invention. The dots indicate selected control points. Stabilization and registration are done by using these control points.

Figure 4:
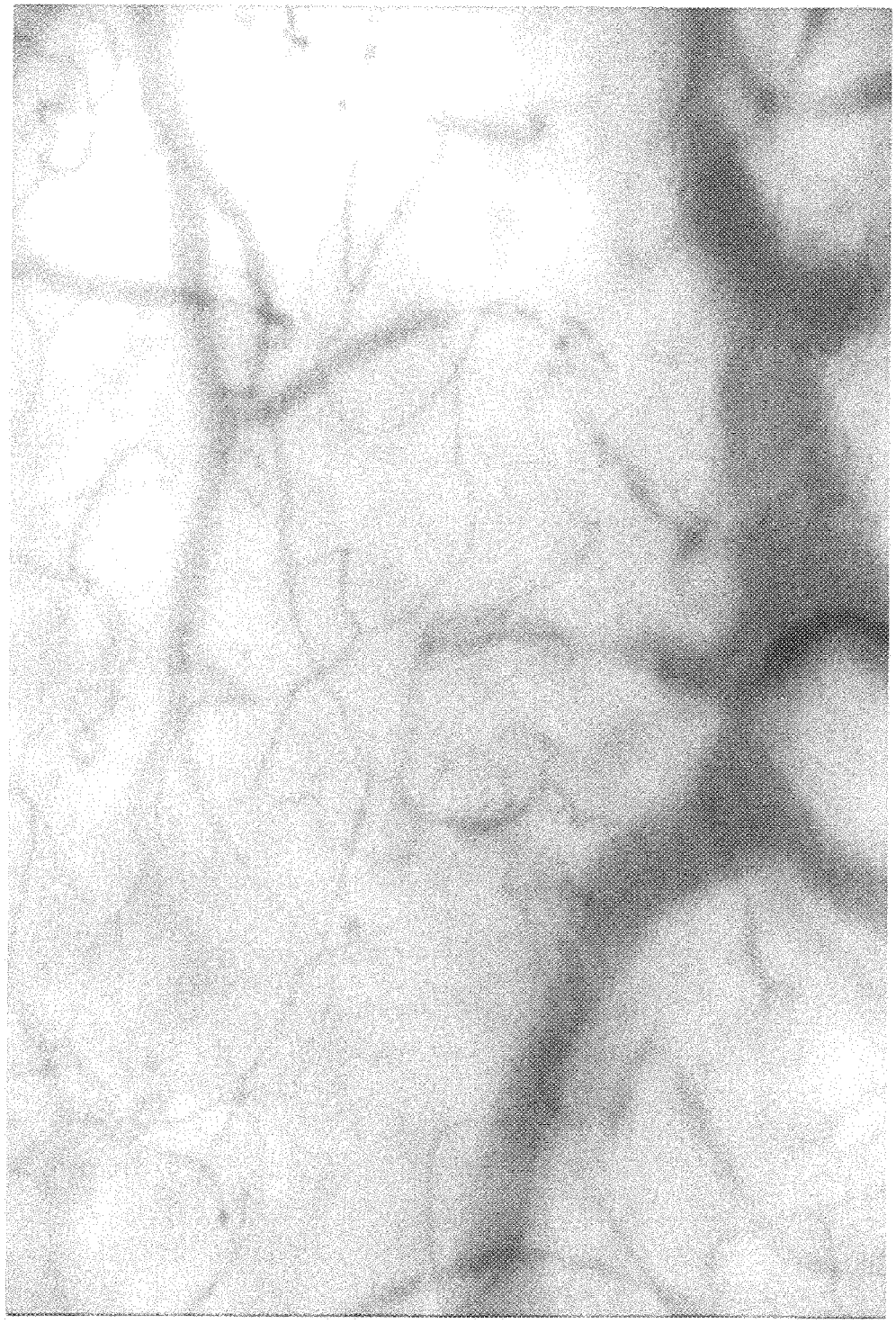
FIG. 4 shows another original video frame of blood vessels from a video of the tongue surface.
Figure 5:
FIG. 5 shows the final result of segmentation on the video frame of FIG. 4 as implemented by an embodiment of the invention.

The results of segmentation indicate that the algorithm extracts the majority of the capillaries and thin blood vessels in a microcirculation image. The segmentation process also extracts many the capillaries that cannot be easily observed by human eye. FIG. 4 shows another original video frame of a capillary image. The result of automatic segmentation as implemented by an embodiment of the invention is shown in FIG. 5.

Figure 6:
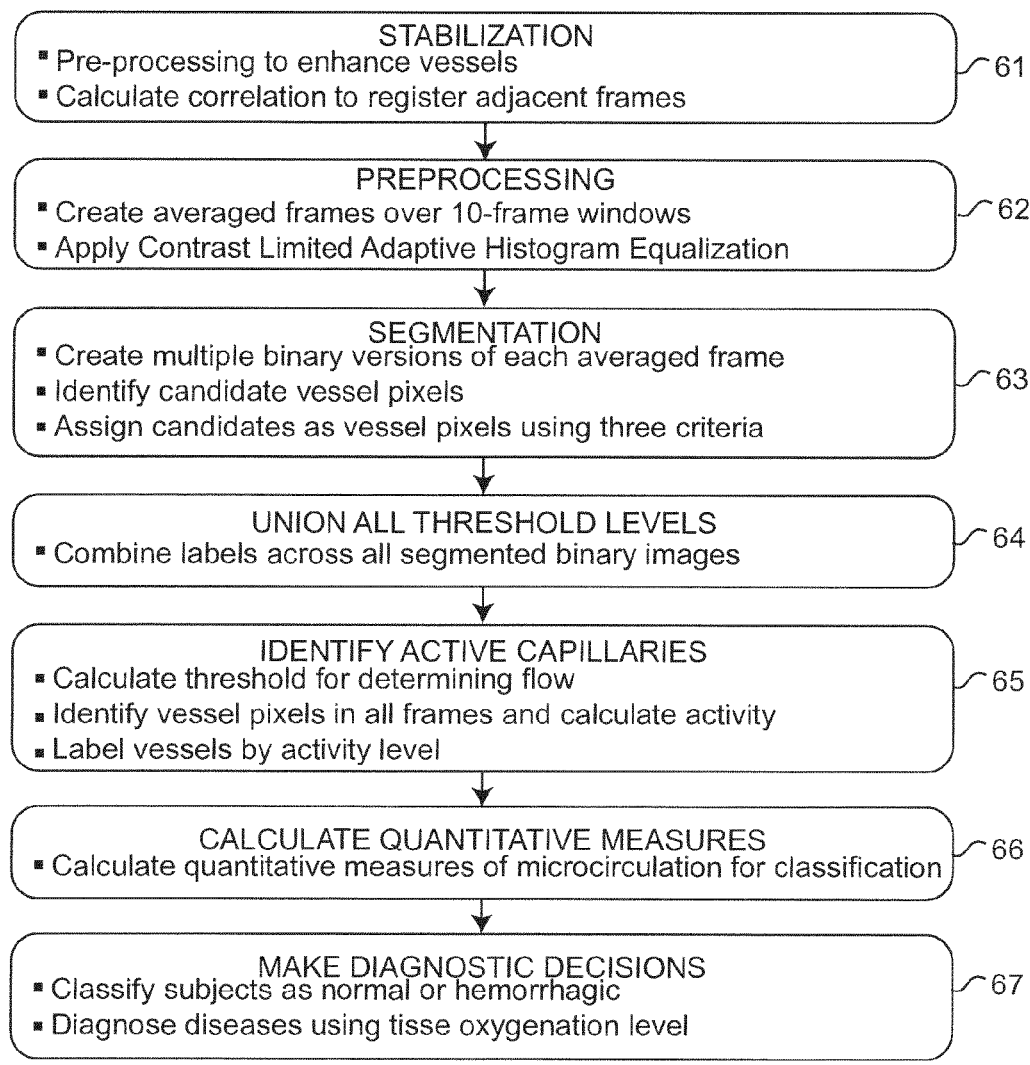
FIG. 6 is a flowchart illustrating the logic of the image processing and machine learning for diagnostic analysis of microcirculation implemented according to an embodiment of the invention.

FIG. 6 illustrates to the image processing and machine learning for diagnostic analysis of microcirculation as implemented in an embodiment of the invention. The first process 61 is video stabilization. This has two main components, pre-processing to enhance vessels, and calculating correlation to register adjacent frames. The next process 62 is another pre-processing step which first creates averaged frames over ten-frame windows and then uses contrast limited adaptive histogram equalization. Next, in segmentation process 63, the first step is to create multiple binary versions of each averaged frame. Next, candidate vessel pixels are identified. Then, a pixel is assigned as a vessel if it meets three criteria, described in more detail hereinafter. In process 64, the union results of all threshold levels is computed. This is followed in process 65 by identification of active capillaries. This process has as the first step the calculation of threshold for determining flow. Next, the pixels assigned as vessels in all frames are identified and their activity calculated. Then, the vessels are labeled by activity level. In process 66, quantitative measures of microcirculation are calculated for classification. Finally, in process 67, diagnostic decisions are made. This is done by first classifying subjects as normal or hemorrhagic, followed by dagnosing diseases using tissue oxygenation level. The results are displayed on display 14, shown in FIG. 1, as a decision-support system for the physician.

Figure 7:
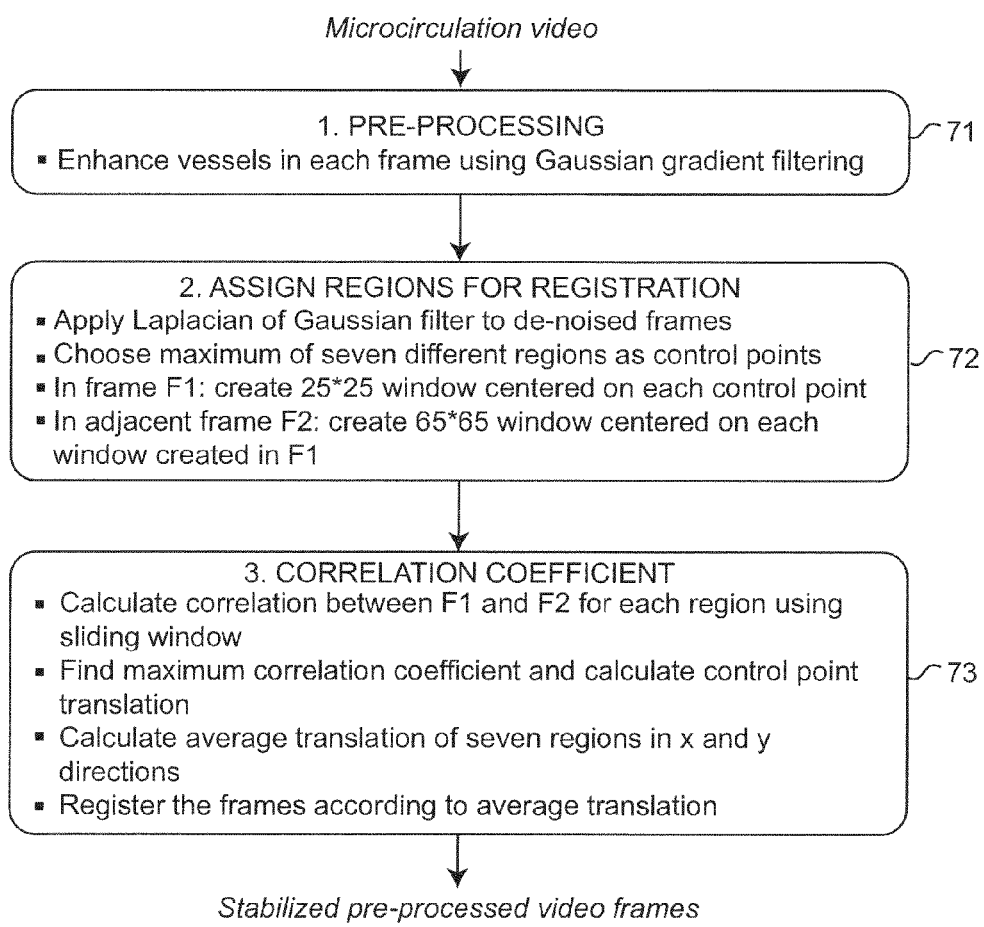
FIG. 7 is a flowchart illustrating in more detail the logic of the stabilization performed by the process shown in FIG. 6.

Each of the foregoing processes broadly described with reference to FIG. 6 will now be described in more detail. Considering first the process 61 of stabilization shown in FIG. 6, reference is made to FIG. 7. The microcirculation video is input to the pre-processing stage 71. In this stage, Gaussian gradient filtering is used to enhance the contrast of the blood vessels in each video frame, making them easier to identify. First, a two dimensional (2D) Gaussian smoothing kernel is convolved with the stabilized video frame to reduce noise. The 2D Gaussian function is given by:

$$G(x, y, \sigma) = \frac{1}{2\pi\sigma^2} e^{\frac{-(x^2+y^2)}{2\sigma^2}}$$

The kernel's degree of smoothing is determined by the standard deviation $\sigma$. In the embodiment of the invention, $\sigma=2$ is used for this step.

The blood vessels in the video frames are much darker than their background and can be characterized by a large and sudden change in grey-level intensity of the pixels; in other words, a large and sudden change in the gradient. Treating the image I as a 2D function, the algorithm calculates the partial first-order derivatives of I in the x and y directions. These approximate derivatives are combined to form the gradient magnitude:

$$I(x, y) = \sqrt{\left(\frac{dG(x, y, \sigma)}{dx}\right)^2 + \left(\frac{dG(x, y, \sigma)}{dy}\right)^2}$$

The gradient magnitude values for each pixel in I are used to generate a gradient filtered version of the original image. The blood vessels will appear very bright against a dark background.

After the pre-processing stage 71, the next stage 72 involves assigning regions for correlation. Movement artifacts in the video caused by the subject or imaging device can lead to image instability, making vessel detection difficult. To avoid this, the video sequence must be stabilized. This is done by identifying control points on capillaries and tracking them through adjacent frames, starting with the first frame of the video, then performing registration. The transform between two adjacent frames can be calculated using these control points, which are automatically selected by applying a Laplacian of Gaussian filter to the image. This uses Gaussian smoothing to reduce noise (as described above) then calculates the Laplacian of the result. Formally, the Laplacian L of an image I is given by:

$$L(x, y) = \frac{\partial^2 I}{\partial x^2} + \frac{\partial^2 I}{\partial y^2}$$

In other words, the Laplacian is the $2^{nd}$ order derivative of the image. One control point is selected from each of seven predefined regions in L, covering separate areas of the image.

To align two adjacent frames $F_1$ and $F_2$, the algorithm first defines seven 25×25 pixel windows $D_i$ in frame $F_1$, each centered on one of the control points $C_i$ (i=1, ..., 7). in frame $F_2$, seven 65×65 windows $W_i$ are created, each centered on one of the 25×25 sub-windows $D_i$ in frame $F_1$.

The next stage 73 calculates the correlation between frames $F_1$ and $F_2$ for each region using a sliding window. By sliding a 25×25 sub-window $D_i$ around each window $W_i$ in turn and calculating the correlation coefficient with the corresponding sub-window $D_i$ in frame $F_1$ at each point, the algorithm finds the maximum correlation coefficient for each region. The correlation coefficients are calculated according to the formula:

$$R(i, j) = \frac{C(i, j)}{\sqrt{C(i, i)C(j, j)}}$$

where C is the covariance matrix, calculated as:

$$cov(x_1, x_2) = E[(x_1-\mu_1)(X_2-\mu_2)]$$

Here, E is the expectation operator and $\mu_1 = E(x_1)$.

Each diagonal element R(i, i) in the matrix R has value 1. The maximum correlation coefficient is recorded for each of the seven regions. The amount of translation between frames $F_1$ and $F_2$ is then taken as the maximum of these seven coefficients, and used to register the two frames. This process of matching adjacent frames continues throughout the video.

Figure 8:
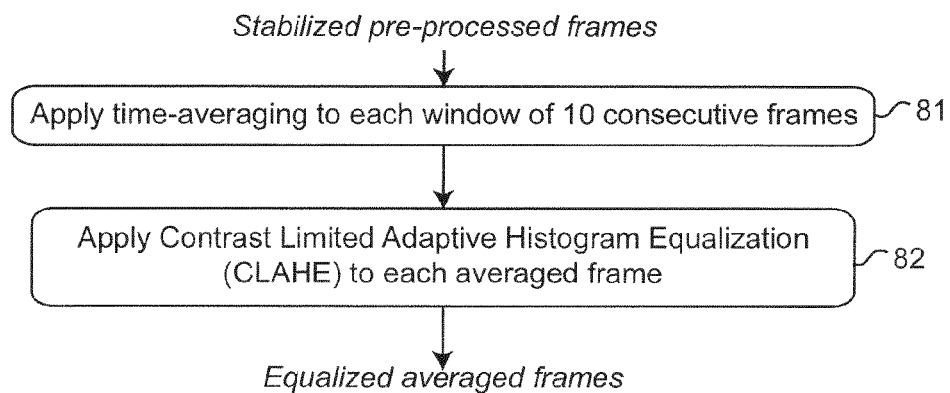
FIG. 8 is a flowchart illustrating in more detail the logic of the pre-processing performed by the process shown in FIG. 6.

The next stage of the image processing shown in FIG. 6 is pre-processing 62. This is shown in more detail in FIG. 8. Here, stabilized pre-processed video frames are input. The raw microcirculation videos are captured at a rate of 30 frames/second. After stabilization, the video is split into windows of ten consecutive frames. To reduce noise and assist in identifying capillaries as continuous structures, each window is used to create a new averaged frame F, where each pixel in F is calculated as the arithmetic average of the same location's intensity value across the entire ten-frame window.

Next, in step 82, Contrast Limited Adaptive Histogram Equalization (CLAHE) is performed on each averaged frame to increase the visibility of blood vessels and capillaries. CLAHE partitions an image into contextual regions and applies histogram equalization to each region in order to even out the overall gray level distribution. This is widely used in imaging software and the full mathematical details of the algorithm can be found in "Contrast Limited Adaptive Histogram Equalization" (Karel Zuiderveld, Academic Press Graphics Gems Series, Graphics Gems IV, pp. 474-485 1994). The output is a sequence of pre-processed averaged frames, each covering a window of ten consecutive frames in the microcirculation video which are input to the segmentation stage 63 of the imaging processing shown in FIG. 6.

Figure 9:
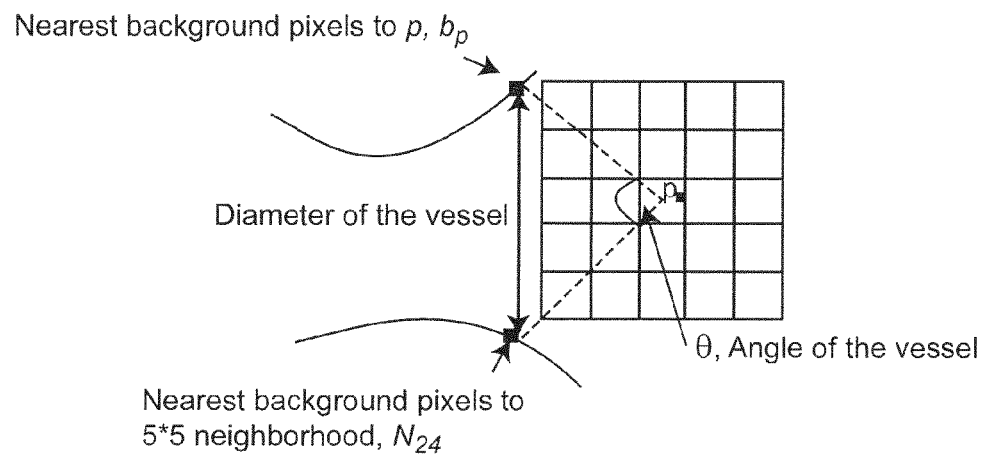
FIG. 9 is a graphical representation of the segmentation process performed by the process shown in FIG. 6.

FIG. 9 graphically illustrates the geometric parameters used in the process of segmentation. Segmentation is applied to each averaged frame. Pixel p is the vessel candidate. The nearest background pixel to p is shown by $b_p$. The diameter of the vessel is the maximum value of the distance between $b_p$ and the background pixels of 5×5 neighborhood, $N_{24}$. The angle of the vessel is calculated as the angle between bp and $N_{24}$.

Figure 10:
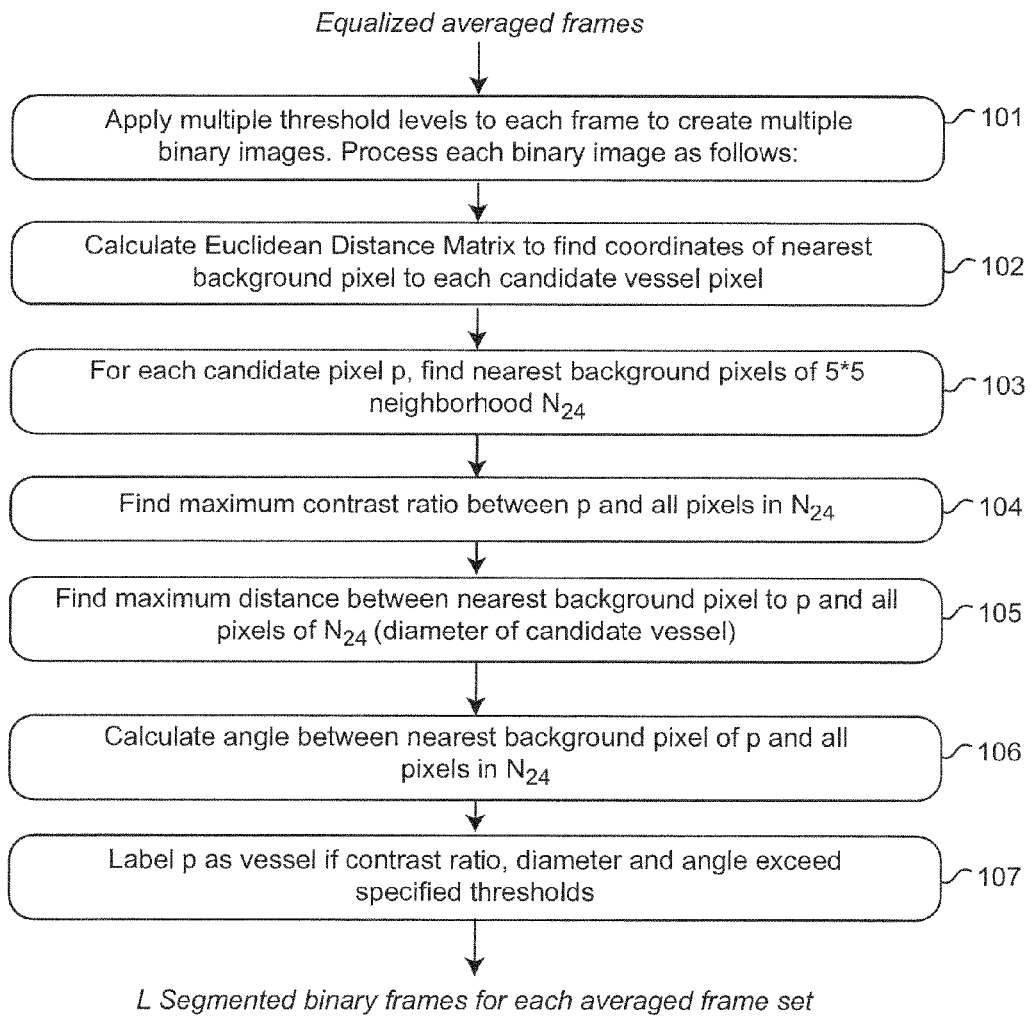
FIG. 10 is a flowchart showing in more detail the logic of the segmentation process illustrated in FIG. 9 and performed by the process shown in FIG. 6.

With this background, reference is now made to FIG. 10 which shows in more detail the segmentation process. The input is the sequence of equalized averaged grayscale frames. In the first stage 101, a range of threshold levels is selected, creating one binary image per level for each average frame A. The threshold levels are set by default, but the system allows manual selection as well. These binary images contain candidate vessel pixels. To filter these candidates, the following steps 102 to 107 are then applied to each binary image.

At step 102, a Euclidean distance matrix A is calculated. This matrix represents the spacing of a set of n points in Euclidean space, where the elements are defined as:

$$a_{ij} = \|x_i - x_j\|^2 \quad 0 < i, j \le n$$

The element at A[i j] is the square of the distance between the $i^{th}$ and $j^{th}$ points in the set. A Euclidean distance matrix E is created for the binary image $B_i$ currently being analyzed. This records the distance between each foreground pixel and the nearest background pixel. Note that after the preprocessing step, the foreground pixels in each binary image are the potential vessel pixels. The matrix E is the same size as $B_i$, with E[i j] being the distance of the image pixel at B[i j] to the nearest background pixel in $B_i$. The coordinates of this nearest background pixel are recorded in a second matrix $C_i$, constructed simultaneously. Detailed information on the Euclidean Distance Matrix can be found in "Fast Raster Scan Distance Propagation on the Discrete Rectangular Lattice" (F. Leymarie and M. D. Levine, CVGIP: Image Understanding, vol. 55, issue 1, January 1992).

Reference is made again to FIG. 9 and to step 103 where the nearest background pixels of the 5×5 neighborhood $N_{24}$ is found for each non-background pixel p. Here, p is the current pixel, $b_p$ is the nearest background pixel to p, and $N_{24}$ contains the nearest background pixels to pixel p's 5×5 neighborhood. Based on these parameters, the following three vessel parameters are calculated in steps 104 to 106:

The contrast ratio between pixel p and the pixels in neighborhood $N_{24}$, recording the maximum value of pixel p.
The distance between $b_p$ and the pixels in $N_{74}$ (i.e., the vessel diameter), recording the maximum value of pixel $p_d$.
The angle between $b_p$ and the pixels in neighborhood $N_{24}$ (i.e., the angle of the vessel), recording the maximum value $p_\theta$.

In step 107, a pixel is verified as a vessel if the maximum measures calculated in steps 104 to 106 meet a set of pre-defined criteria:

$p_c > P_c$
$P_d < P_d$
$P_\theta > P_\theta$ where $p_c$, $p_d$ and $p_\theta$ represent the contrast ratio, the vessel diameter and the vessel angle, respectively. In the embodiment of the invention, the pre-defined values are: $P_c$=1.25, $P_d$=18, $P_\theta$=120. This test is applied to each candidate vessel pixel in turn, the result being a label map of identified vessel pixels returned in the form of a binary image. The output is L segmented binary frames for each averaged frame set.

Figure 11:
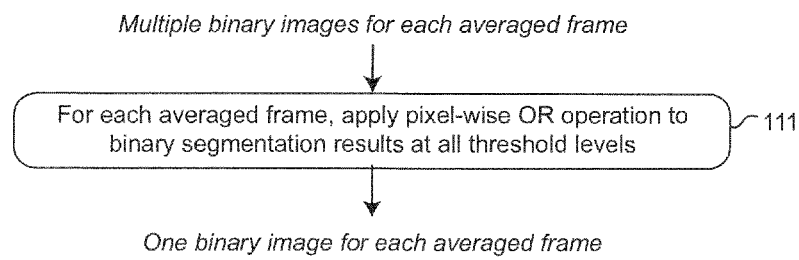
FIG. 11 is a flowchart showing in more detail the logic of the union of results performed by the process shown in FIG. 6.

The next stage 64 in the image processing shown in FIG. 6 is the union results of all threshold levels. This is described in more detail with reference to FIG. 11. the input to this stage are multiple vessel label maps (as binary images) for each member in a set of averaged frames. The previous stage extracted a set of binary images from a single averaged frame by applying multiple thresholds, and detected vessel pixels in each. The resulting vessel binary images are now combined via a pixel-wise OR (union) operation across all threshold levels. The final segmentation result SF is given by:

$$S_F = \bigcup_{i=1}^{L} S_i$$

where L is the number of threshold levels (i.e., the number of segmented binary images returned by the segmentation step for each averaged frame). If a pixel is assigned a vessel label in any of the images $S_i$, it will be assigned a vessel label in $S_F$. The final result of this stage is a single binary image for each averaged frame showing the locations of the vessel pixels.

Figure 12:
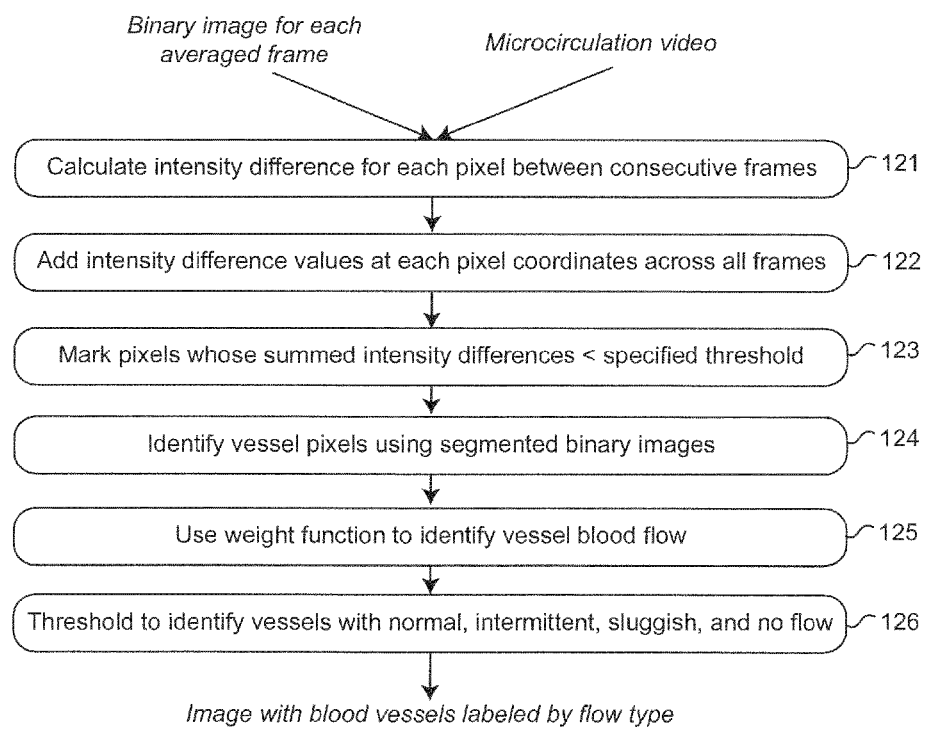
FIG. 12 is a flowchart showing in more detail the logic of the identification of active capillaries performed by the process shown in FIG. 6.

The next stage 65 in the image processing shown in FIG. 6 is the identification of active capillaries. This process is shown in more detail in FIG. 12. The input is the raw microcirculation video and a set of binary images showing identified vessel pixels. In steps 121 and 122, intensity differences are calculated and summed across consecutive frames. Using the raw microcirculation video, an intensity variation matrix is constructed which records how much the intensity value for each pixel location varies throughout the video. For example, consider location [i,j]. The difference in pixel intensity at this location will be calculated over consecutive frames of the video. This results in a three dimensional (3D) matrix of size (frame width×frame height×number of frames in video), which is then summed to create a 2D intensity variation matrix of size (frame width×frame height). This second matrix records much the intensity value varies throughout the video for each pixel.

At step 123, a threshold is applied to the intensity variation matrix to identify vessels without blood-flow. As blood moves through a vessel, the vessel pixels show intensity variation across video frames. A low degree of variation indicates a lack of flow, so pixel locations with variation below the specified threshold are recorded as non-active. The threshold level is automatically calculated using the gray level information of the video, though the system also allows the user to define their own.

At step 124, the binary segmentation images created for each averaged frame are collected into a set covering the entire video. Pixels which are labeled as vessel across the entire set are recorded as true vessel pixels. This followed in step 125 where a weight function is applied to the results of the last two steps to identify active vessels, and generates an output image V showing only the active vessels. Pixel (i, j) of V is defined by:

$$V(i,j) = \alpha S(i,j) + \beta(R(i,j))$$

where α and β are weight variables, S(i, j) is pixel's value in the thresholded intensity variation matrix, and R(i, j) is binary "1" if the pixel was identified as vessel in step 124, and binary "0" otherwise.

The final step 126 classifies the capillaries into two groups (active or passive) based on their level of blood-flow. However, the user may choose to use four groups instead (no flow, sluggish, intermittent, and normal). In this case, multiple threshold levels are applied to the intensity variation matrix in step 123.

Figure 13:
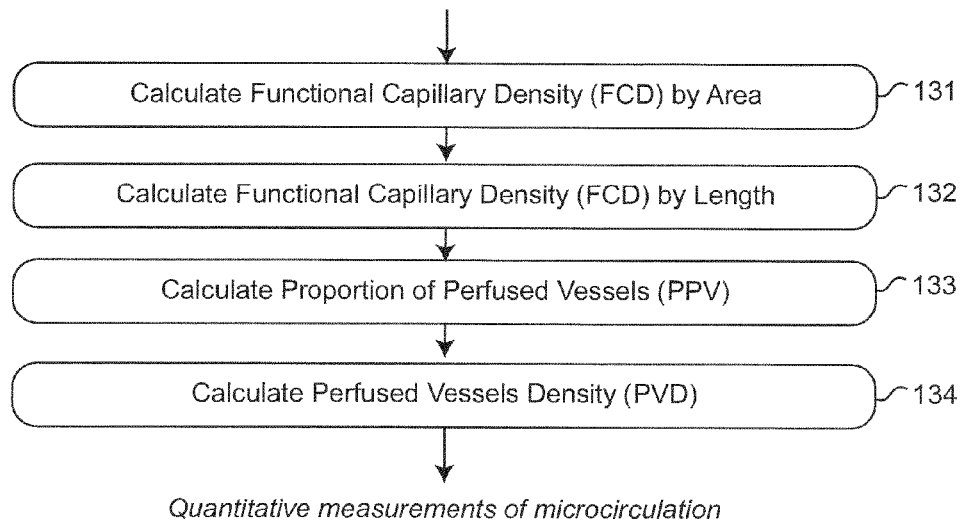
FIG. 13 is a flowchart showing in more detail the logic of calculating parameters performed by the process shown in FIG. 6.

The next stage 86 in the image processing shown in FIG. 6 is the calculation of parameters, and this is shown in more detail in FIG. 13. The input is an image with blood vessels labeled by flow type (e.g., active and passive or no flow, sluggish, intermittent, and normal). In steps 131 to 133, Functional Capillary Density (FCD) is calculated by Area, FCD is calculated by Length, and Proportion of Perfused Vessels (PPV) is calculated. FCD is the primary measure used to evaluate microcirculation. It can be calculated via a manual approach or by using computer software. The manual method involves applying a grid to the video frame and counting the number of vessels which cross the lines of the grid, while the software method calculates the ratio of perfused vessels to the total surface.

The previous stage created an image with blood vessels labeled by group. In this stage, active vessels are counted as those that are normal, intermittent or sluggish. Three measures are obtained: FCD by Area, FCD by Length, and the Proportion of Perfused Vessels (PPV). These are calculated as follows:

$$FCD \text{ By Area} = \frac{A_{av}}{A_v}$$

$$FCD \text{ By Length} = \frac{L_{av}}{L_v}$$

$$PPV = \frac{N_{av}}{N_v}$$

where:
$A_{av}$ is the total area covered by the active vessels
$A_v$ is the total area covered by all vessels
$L_{av}$ is the total length of the active vessels
$L_v$ is the total length of all vessels
$N_{av}$ is the total number of active vessels
$N_v$ is the total number of all vessels.

The final quantitative measure, Perfused Vessel Density (PVD), is calculated in step 154 as:

$$PVD=PCD*PPV$$

Figure 14:
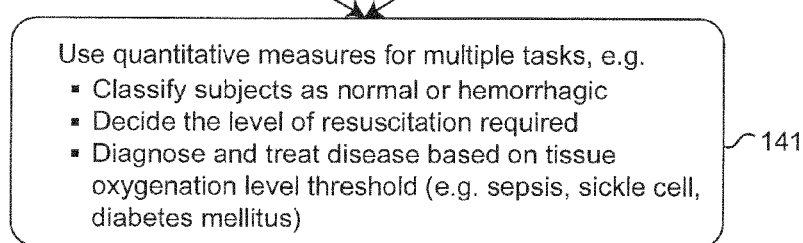
FIG. 14 is a flowchart showing in more detail the logic of making diagnostic decisions performed by the process shown in FIG. 6.

The next stage 67 in the image processing of FIG. 6 is making diagnostic decisions. This process is shown in more detail in FIG. 14. The input is the level of tissue oxygenation for a patient (based on quantitative measures extracted from microcirculation video). Three general areas of application are considered at step 141:

Classifying subjects as normal or hemorrhagic. Hemorrhaging subjects can be identified by their Functional Capillary Density (FCD) values; subjects with FCD below a certain threshold level are considered to be hemorrhaging.

Deciding the level of resuscitation required for a patient. Patients with certain injuries and conditions tend to require intravenous fluid resuscitation; for example, hemorrhagic subjects requiring blood infusion, or burn victims. The level of resuscitation can have considerable impact on patient outcome, with both over and under resuscitation being harmful. Determining the correct level and maintaining it over time can be challenging. However, the level of tissue oxygenation provides valuable information on in this task. Therefore, our system's ability to automatically analyze videos and calculate FCD values in real-time can assist physicians in deciding when to start and stop resuscitation.

Diagnosis and treatment of diseases. For example, various diseases affect the body's level of tissue oxygenation level, including sepsis, chronic ulcers, diarrhea, diabetes mellitus, sickle cell, and hypertension. Via machine learning techniques, measures extracted from a new patient's microcirculation video can be used to assist physicians in diagnosis.

Oxygenation level threshold varies for different diseases such as sepsis, chronic ulcers, diarrhea, diabetes mellitus, sickle cell, and hypertension. By training the system with a certain number of samples, a decision-support system can be implemented for each disease.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A computer implemented process for the diagnostic analysis of microcirculation, comprising the steps of:
obtaining video images of microvasculature from tissue surface videos;
stabilizing by computer the obtained video images to eliminate motion artifacts;
segmenting by computer blood vessels from each video frame of stabilized video images to provide quantitative and qualitative measure of microcirculation;
identifying by computer active capillaries in stabilized and segmented images and labeling blood vessels as to quality of flow;
calculating by computer Functional Capillary Density (FCD) and Proportion of Perfused Vessels (PPV) in identified active capillaries; and
based on calculated FCD and PPV, classifying by computer subjects as normal or hemorrhagic.

2. The computer implemented process for the diagnostic analysis of microcirculation according to claim 1, wherein the step of stabilizing comprises the steps of:
identifying video frames which are in transition; and
using block matching and correlation methods to match blocks in video frames that include only objects of interest.

3. The computer implemented process for the diagnostic analysis of microcirculation according to claim 1, wherein the step of identifying active capillaries labels blood vessels as normal, intermittent, sluggish and zero flow.

4. The computer implemented process for the diagnostic analysis of microcirculation according to claim 1, wherein the step of identifying active capillaries uses original video frames and segmentation of averaged frames to automatically detect blood vessels without flow.

5. The computer implemented process for diagnostic analysis of microcirculation according to claim 1, further comprising the step of diagnosing by computer diseases using calculated quantitative parameters of microcirculation.

6. The computer implemented process for diagnostic analysis of microcirculation according to claim 5, wherein the step of pre-processing the video images to stabilize images comprises the steps of:

calculating by computer a gradient using first order derivative of Gaussian; and applying by computer digital two dimensional (2D) wavelet transform to the video images.

7. The computer implemented process for diagnostic analysis of microcirculation according to claim 1, wherein the step of stabilization comprises the steps of:

enhancing by computer vessels in each frame using Gaussian gradient filtering;

assigning by computer regions for correlation by applying a Laplacian filter to the pre-processed image;

calculating by computer the maximum filtered image in a plurality of different blocks of the frame;

drawing by computer a plurality of m×m rectangles whose centers are the maximums in a first frame;

drawing by computer a plurality of n×n rectangles as windows, n>m, around the m×m rectangles in a next consecutive frame;

calculating correlation coefficients by computer between a region selected from the first frame m×m rectangle from an n×n window selected in the next consecutive frame;

sliding by computer the m×m rectangle from the second region by one pixel in the whole n×n window to find the maximum correlation coefficient;

repeating the steps of calculating correlation coefficients and sliding for all blocks;

averaging by computer the translation of all regions in x and y directions separately; and registering by computer the frames according to a calculated translation amount to produce a stabilized microcirculation video.

8. The computer implemented process for diagnostic analysis of microcirculation according to claim 1, wherein the step of pre-processing comprises the steps of:

applying by computer time-averaging to each of a plurality of consecutive frames; and applying by computer Contrast Limited Adaptive Histogram Equalization (CLARE) to produce greyscale pre-processed frames.

9. The computer implemented process for diagnostic analysis of microcirculation according to claim 8, wherein the step of segmenting comprises the steps of:

inputting the pre-processed grayscale frames;

applying by computer multiple threshold levels to the pre-processed greyscale frames;

entering a computer processing loop so that each binary image is processed in turn;

calculating by computer the Euclidean distance matrix, resulting in two M×N matrices, the first of these two matrices having a distance value to the nearest background for each pixel, and the second matrix having coordinates of the nearest background;

finding by computer the nearest background pixels of a k×k neighborhood $N_i$ for each non-background pixel p;

calculating by computer the contrast ratio of pixel p and neighborhood $N_i$;

comparing by computer the maximum of the contrast ratio with a predefined value $P_c$;

calculating by computer a distance from the nearest background pixel of p and neighborhood $N_i$;

comparing by computer a maximum of the distance which is the diameter of the vessel to the maximum value with a predefined value $P_d$;

calculating by computer an angle between the nearest background pixel of p and neighborhood $N_i$;

comparing by computer the maximum value of the angle with a predefined value $P_\theta$;

for each vessel candidate pixel p, the pixel is verified as a vessel if (1) the contrast ratio is greater than $P_c$, (2) the diameter is less than $P_d$, and (3) the angle is greater than $P_\theta$; and determinating by computer whether all binary images have been processed and, if so, then for each averaged frame, there will be L number of segmented binary images, where the number of threshold levels is L, and the final output is the segmented binary frames.

10. The computer implemented process for diagnostic analysis of microcirculation according to claim 9, wherein the step of identification of active capillaries comprise the steps of:

calculating by computer a pixel by pixel difference of intensity values for consecutive frames, resulting in a three dimensional (3D) matrix, width×height×number of frames;

adding by computer the difference of intensity values at each pixel coordinate, resulting in a two dimensional (2D) matrix; width×height;

finding by computer the pixels segmented as a vessel for all averaged frames;

finding by computer and marking the coordinates of pixels whose summation of the difference of their intensity values are below a defined threshold level;

adding by computer a weight function to the steps of finding to determine vessels without flow; and using by computer different threshold values to determine the vessels with normal flow, intermittent flow, sluggish flow, and no flow to output an image with blood vessels labeled as normal, intermittent, sluggish and zero flow.

11. The computer implemented process for diagnostic analysis of microcirculation according to claim 1, wherein the video images of microvasculature are obtained from the lingual surface.

12. A computer implemented decision support system for the diagnostic analysis of microcirculation, comprising:

video means for obtaining video images of microvasculature from tissue surface videos;

analog-to-digital converter means for converting the video images obtained by said video means to digital video images;

a computer receiving the digital video images, said computer being programmed to pre-process the digital video images to stabilize images between consecutive frames of the tissue surface video, segment each video frame of stabilized video images to provide quantitative and qualitative measure of blood vessels, identify active capillaries in stabilized and segmented images and labeling blood vessels as normal, intermittent, sluggish and zero flow, calculate Functional Capillary Density (FCD) and Proportion of Perfused Vessels (PPV) in identified active capillaries, based on calculated FCD and PPV, classify subjects as normal or hemorrhagic stage, and diagnose diseases using calculated quantitative parameters of microcirculation; and display means for displaying a classification of a subject as normal or hemorrhagic stage and, if hemorrhagic stage, displaying a diagnosis of disease.

* * * * *